(12) United States Patent
Schmuckli et al.

(10) Patent No.: US 11,202,638 B2
(45) Date of Patent: Dec. 21, 2021

(54) SAW GEAR SET

(71) Applicant: Synthes GmbH, Oberdorf (CH)

(72) Inventors: Nils Schmuckli, Sissach (CH); Stefan Gisler, Wallbach (CH); Markus Hermann, Laupersdorf (CH); Robert Goossen, Niederdorf (CH); Martin Muench, Liestal (CH)

(73) Assignee: SYNTHES GMBH, Oberdorf (CH)

( * ) Notice: Subject to any disclaimer, the term of this patent is extended or adjusted under 35 U.S.C. 154(b) by 287 days.

(21) Appl. No.: 16/305,994

(22) PCT Filed: Jun. 13, 2016

(86) PCT No.: PCT/CH2016/000088
§ 371 (c)(1),
(2) Date: Nov. 30, 2018

(87) PCT Pub. No.: WO2017/214737
PCT Pub. Date: Dec. 21, 2017

(65) Prior Publication Data
US 2019/0290289 A1    Sep. 26, 2019

(51) Int. Cl.
*A61B 17/14*    (2006.01)
*A61B 17/42*    (2006.01)
*B27B 19/00*    (2006.01)
*A61B 17/00*    (2006.01)

(52) U.S. Cl.
CPC .......... *A61B 17/142* (2016.11); *B27B 19/006* (2013.01); *A61B 17/14* (2013.01); *A61B 17/144* (2016.11); *A61B 17/42* (2013.01); *A61B 2017/00477* (2013.01)

(58) Field of Classification Search
CPC ..... A61B 17/14; A61B 17/142; A61B 17/144; A61B 2017/320028; A61B 17/42; A61B 2017/00477; B27B 19/006
See application file for complete search history.

(56) References Cited

U.S. PATENT DOCUMENTS

| 3,978,862 A * | 9/1976 | Morrison ............. B23D 49/165 |
| | | 606/178 |
| 5,382,249 A | 1/1995 | Fletcher |
| 5,735,866 A | 4/1998 | Adams et al. |

(Continued)

FOREIGN PATENT DOCUMENTS

| CN | 102133122 | 7/2011 |
| CN | 203576588 U | 5/2014 |

(Continued)

*Primary Examiner* — Zade Coley
*Assistant Examiner* — Diana Jones

(57) ABSTRACT

A saw gear set comprising a set of saw blades and a saw drive (1), wherein each saw blade of the set is configured to be coupled to the saw drive (1) by means of a coupling mechanism (100), which coupling mechanism (100) is configured to transmit a driving force of the saw drive (1) to the saw blade in a force transmission point, for oscillating the saw blade around a pivot axis (300). Each saw blade of the set is configured to be pivotably borne around the pivot axis (300). In operation, an oscillation angle ($\alpha$) around the pivot axis (300) is different for each saw blade of the set depending on a pivot distance between the pivot axis (300) and the force transmission point which varies for each saw blade of the set.

7 Claims, 10 Drawing Sheets

(56) References Cited

U.S. PATENT DOCUMENTS

| | | | |
|---|---|---|---|
| 5,846,244 A | 12/1998 | Cripe | |
| 8,672,943 B2 * | 3/2014 | Fisher | A61B 17/142 |
| | | | 606/82 |
| 9,232,949 B2 * | 1/2016 | Carusillo | A61B 17/142 |
| 2008/0027449 A1 * | 1/2008 | Gundlapalli | A61B 17/1624 |
| | | | 606/82 |
| 2010/0292701 A1 | 11/2010 | Fisher et al. | |
| 2012/0143196 A1 | 6/2012 | Kim | |
| 2012/0289963 A1 | 11/2012 | Legrand et al. | |

FOREIGN PATENT DOCUMENTS

| | | |
|---|---|---|
| CN | 103860232 | 6/2014 |
| DE | 4024235 A1 | 2/1992 |
| DE | 102008062880 A1 | 6/2010 |
| EP | 1882538 A2 | 1/2008 |
| EP | 1740104 B1 | 11/2009 |
| EP | 1880682 B1 | 4/2010 |
| EP | 1974679 B1 | 12/2010 |
| EP | 2011444 B1 | 9/2012 |
| JP | H11-512624 | 11/1999 |
| JP | 200829848 | 2/2008 |
| JP | 2013-71373 | 4/2013 |
| WO | WO 2011/162736 | 12/2011 |
| WO | WO 2012/151122 | 11/2012 |

\* cited by examiner a)

b)

a)

b)

a)

b)

a)

b)

c)

SAW GEAR SET

CROSS REFERENCE TO RELATED APPLICATION

This application is a national stage application of International Patent Application No. PCT/CH2016/000088, filed Jun. 13, 2016. The complete disclosure of the aforementioned related patent application is hereby incorporated herein by reference for all purposes.

TECHNICAL FIELD

The present invention relates to a saw gear set and a use thereof, a set of saw blades, and a saw drive.

BACKGROUND ART

Osteotomy is a surgical treatment involving the cutting of bones, e.g. for shorten or lengthen a bone or for replacing joints. To perform such surgical treatment, specialized tools are required, in particular tools for performing accurate and precise surgery e.g. to prevent the infringement of soft tissue, which infringement could lead to serious complications in the affected area of the bone.

A state of the art tool to perform such osteotomy surgery is a handheld oscillating bone saw gear with a saw drive and a saw blade for cutting the particular bone. An oscillation angle of the saw blade for such a tool is constant and is given by the saw drive which transmits the oscillation to the saw blade. The arc length of the oscillation motion of a distal end of the saw blades, where the serrated distal end of the saw blade is hitting the bone, can only be varied by mounting a shorter or longer saw blade to the saw drive. Therefore it is difficult to precisely adjust the arc length of the oscillation motion of the saw blade, which might be required in surgery for preventing injury.

Therefore, a further state of the art saw gear for osteotomy comprises a saw drive and a saw blade, wherein the saw drive allows to adjust the oscillation angle, such that the saw blade oscillates within the particular oscillation angle. The application of this saw gear requires careful selection of the particular saw blade for the respective oscillation angle. A long saw blade in combination with a large oscillation angle can lead to strong vibrations of the saw blade and therefore to high loads for the oscillation drive which might lead to failure of the saw gear.

DISCLOSURE OF THE INVENTION

The problem to be solved by the present invention is therefore to provide a saw gear set and a use thereof, a set of saw blades, and a saw drive which overcome the disadvantages of the state of the art.

This problem is solved by the subjects of the independent claims.

Accordingly, a first aspect of the invention relates to a saw gear set comprising a set of saw blades and a saw drive, wherein each saw blade of the set is configured to be coupled to the saw drive by means of a coupling mechanism. The coupling mechanism is configured to transmit a driving force of the saw drive to the saw blade in a force transmission point, for oscillating the saw blade around a pivot axis. Each saw blade of the set is configured to be pivotably borne around the pivot axis. In operation, an oscillation angle around the pivot axis is different for each saw blade of the set depending on a pivot distance between the pivot axis and the force transmission point which varies for each saw blade of the set. The oscillation angle thereby refers to an angle of oscillation of a distal end of the saw blade.

Preferably, the saw gear set is a handheld tool for surgery, in particular for osteotomy, wherein the oscillation angle of each saw blade of the set of saw blades is dependent on the respective pivot distance and therefore provides ease adjustment of the oscillation angle by means of selecting the appropriate saw blade of the set.

Preferably, the oscillation angle of each saw blade of the set of saw blades differs for each saw blade solely depending on the pivot distance. In particular, the oscillation angle for a saw blade of the set with a shorter pivot distance is larger than the oscillation angle of a saw blade of the set with a longer pivot distance.

Preferably, each saw blade of the set of saw blades has each a longitudinal axis from a proximal end to a distal end of the blade, wherein the proximal end is directed towards the saw drive and the distal end is directed away from the saw drive. Preferably, the distal end is serrated for sawing.

In a preferred embodiment, all saw blades of the set are of the same length, width and/or thickness. The length refers to an extension of the saw blade from the proximal end to the distal end of each blade. The width of the saw blade refers to an extension of the saw blade in a direction perpendicular to the longitudinal axis.

If all the saw blades of a set are of the same length and width, the distal end of each saw blade oscillates over an arc length with depends on the oscillation angle and therefore depends on the pivot distance of the respective saw blade.

In a further preferred embodiment, at least two saw blades of the set are of different length, wherein preferably, the longer saw blade has a smaller oscillation angle than the shorter saw blade. The saw blades of the set can be of different width.

A preferred coupling mechanism of the saw gear set comprises an outer contour, in particular a circular section, of the saw blade mating a saw blade guide of the saw drive.

Another preferred coupling mechanism of the saw gear set comprises a drive pin mating a slot.

In a preferred embodiment, a drive pin of the saw drive transmits the driving force of the saw drive to the saw blade for oscillating the saw blade around the pivot axis, wherein the force transmission point is therefore located between the drive pin and the slot.

In another embodiment it is further preferable, that the slot transmits the driving force of the saw drive to a pin of the saw blade, for oscillating the saw blade around the pivot axis.

In a preferred embodiment, the driving force is a preferably oscillating rotational force acting on the saw blade, preferably oscillating within 1°-10° around a pivot axis, which preferably oscillating driving force is translated into a preferably oscillating rotation of the distal end of the saw blade around its pivot axis.

In a further preferred embodiment, the driving force is a preferably oscillating translational force acting on the saw blade in a direction perpendicular to the longitudinal axis of the saw blade and perpendicular to the pivot axis, which preferably oscillating driving force is translated into a preferably oscillating rotation of the distal end of the saw blade around its pivot axis.

A preferred embodiment of the saw gear set of the invention comprises a first saw blade with a first pivot axis in a first position having a first pivot distance to obtain a first oscillation angle, and a second saw blade with a second pivot axis in a second position having a second pivot distance to obtain a second oscillation angle.

In a further preferred embodiment of the saw gear set, the saw drive comprises a first and a second drive pin. The first and the second drive pin are preferably two separate parts, but can also be formed as one part. A first saw blade comprises a first slot arrangement with a first portion and a second portion, which first slot arrangement encloses the first and the second drive pin. The first portion and the second portion of the first slot arrangement can be separate slots or can be fused slots. The first drive pin interlocks with the first portion of the first slot arrangement, for transmitting the driving force of the saw drive to the first saw blade in a first force transmission point, to obtain a first oscillation angle. A second saw blade comprises a second slot arrangement with a third portion and a fourth portion, which second slot arrangement encloses the first and the second drive pin. The third portion and the fourth portion of the second slot arrangement can be separate slots or can be fused slots. The second drive pin interlocks with the fourth portion of the second slot arrangement for transmitting the driving force of the saw drive to the second saw blade in a second force transmission point, to obtain a second oscillation angle. In particular, a cross-section area of the first portion of the first slot arrangement is smaller than the cross-section area of the second portion of the first slot arrangement. In particular, a cross-section area of the third portion of the second slot arrangement is larger than the cross-section area of the fourth portion of the second slot arrangement.

In a further preferred embodiment of the saw gear set, in response to applying the driving force, the second drive pin freely oscillates within the second portion of the first slot arrangement. Furthermore, in response to applying the driving force, the first drive pin can freely oscillate within the third portion of the second slot arrangement.

In a further preferred embodiment of the saw gear set, the driving force is a preferably oscillating translational force, preferably oscillating within a distance of 1-10 mm, acting on the saw blade in a direction parallel to the longitudinal axis of the saw blade which preferably oscillating driving force is translated into a preferably oscillating rotation of the distal end of the saw blade around its pivot axis.

In a further preferred embodiment of the saw gear set, each saw blade of the set comprises a slot in form of a recess, in particular a longitudinal recess, in particular extending to the proximal end of the saw blade of the set. A first angle between a longitudinal axis of a first recess and the longitudinal axis of the first saw blade defines a first force transmission point, to obtain a first oscillation angle around the pivot axis. A second angle between a longitudinal axis of a second recess and the longitudinal axis of the second saw blade defines a second force transmission point, to obtain a second oscillation angle around the pivot axis.

In a further preferred embodiment of the saw gear set, each saw blade has a slot that is a curved recess, preferably extending to a proximal end of the saw blade, wherein a radius of the curved slot defines the force transmission point, to obtain the oscillation angle around the pivot axis.

In a further preferred embodiment of the saw gear set, the saw drive comprises the slot, wherein a first saw blade of the set comprises a first drive pin positioned at a first pivot distance from the pivot axis to obtain a first oscillation angle. A second saw blade of the set comprises a second drive pin positioned at a second pivot distance from the pivot axis to obtain a second oscillation angle.

A second aspect of the invention relates to a set of saw blades, wherein each saw blade is couplable to a saw drive by means of a coupling mechanism for transmitting a driving force from a saw drive to the blade in a force transmission point. A preferred coupling mechanism is thereby a drive pin mating a slot. A further preferred coupling mechanism comprises an outer contour of the saw blade, in particular a circular section, mating a saw blade guide of the saw drive. Each saw blade of the set is pivotable mountable around a pivot axis. In operation, an oscillation angle around the pivot axis is different for each saw blade of the set depending on a pivot distance between the pivot axis and the force transmission point which varies for each saw blade of the set.

A set of saw blades can comprise only one saw blade. Preferably, a set of saw blades comprises at least two saw blades with different pivot distances.

A preferred embodiment of the set of saw blades comprises a first saw blade with a first pivot axis in a first position for obtaining a first pivot distance, for obtaining a first oscillation angle, and a second saw blade with a second pivot axis in a second position for obtaining a second pivot distance, for obtaining a second oscillation angle.

In a further preferred embodiment of the set of saw blades a first saw blade of the set comprises a first slot arrangement with a first and a second portion for enclosing a first and a second drive pin of a saw drive. The first portion is configured to interlock with the first drive pin of the saw drive, for transmitting the driving force of the saw drive to the first saw blade in a first force transmission point for obtaining a first oscillation angle. A second saw blade of the set comprises a second slot arrangement with a third and a fourth portion for enclosing the first and the second drive pin of the saw drive. The fourth portion is configured to interlock with the second drive pin of the saw drive, for transmitting the driving force of the saw drive to the second saw blade in a second force transmission point for obtaining a second oscillation angle. Preferably, relating to the first blade, the first portion has a smaller cross-sectional area than the second portion, which first and second portion are preferably rectangular. Furthermore, relating to the second blade, the third portion can have a larger cross-sectional area than the fourth portion, which third and fourth portion are preferably rectangular. In this embodiment, the saw gear set preferably contains only one pivot axis, which is at the same position for all saw blades of the set.

In a further preferred embodiment of the set of saw blades, each saw blade comprises a slot for mating a drive pin for converting a preferably oscillating translational driving force parallel to the longitudinal axis of the saw blade into a preferably oscillating rotation around the pivot axis.

Preferably, the slot is in form of a recess, in particular a longitudinal recess, which preferably extends to the proximal end of each saw blade of the set of saw blades, very preferably opens to the proximal end of the saw blade. A first angle, of preferably below 20°, between a longitudinal axis of a first recess and the longitudinal axis of the first saw blade defines a first force transmission point, to obtain a first oscillation angle around the pivot axis. A second angle, of preferably below 45° between a longitudinal axis of a second recess and the longitudinal axis of the second saw blade defines a second force transmission point, to obtain a second oscillation angle around the pivot axis.

In a further preferred embodiment of the set of saw blades, each saw blade of the set comprises a slot in the form of a curved recess, preferably extending to a proximal end of the saw blade, wherein a radius of the slot defines the force transmission point, to obtain the oscillation angle around the pivot axis. Each saw blade of the set can have a curved recess with a different radius to obtain different oscillation angles around the pivot axis.

In a further preferred embodiment of the set of saw blades, the first saw blade comprises a first drive pin in a first position, for coupling to a mating slot of the saw drive. The second saw blade comprises a second drive pin in a second position, for coupling to the mating slot of the saw drive. The pivot distance of the first saw blade is longer than the pivot distance of the second saw blade. The saw drive transmits a rotational driving force to the slot and therefore to the saw blade, such that the oscillation angle of the saw blade with the longer pivot distance is smaller than the oscillation angle of the saw blade with the larger pivot distance.

A third aspect of the invention relates to a saw drive for oscillating a saw blade of the set of saw blades, which is configured to be pivotably borne around a pivot axis, comprising a coupling mechanism for coupling to the saw blade. The coupling mechanism is configured to transmit a driving force of the saw drive to the saw blade in a force transmission point. An oscillation angle of the saw blades is different for each saw blade, depending on a pivot distance between the force transmission point and the pivot axis of the saw blades, which varies for each saw blade of the set. A preferred coupling mechanism is thereby a drive pin mating a slot. A further preferred coupling mechanism comprises an outer contour of the saw blade, in particular a circular section, mating a saw blade guide of the saw drive.

A preferred embodiment of the saw drive is configured to apply the preferably oscillating driving force as a preferably oscillating rotational force, preferably oscillating within 1°-10° around a pivot axis, to the saw blade of the set of saw blades, which preferably oscillating driving force is translated into a preferably oscillating rotation of the distal end of the saw blade around its pivot axis.

A further preferred embodiment of the saw drive is configured to apply a preferably oscillating driving force as a translational force acting on a saw blade of the set of saw blades in a direction perpendicular to the longitudinal axis of the saw blade and perpendicular to the pivot axis. The driving force is translated into a preferably oscillating rotation of the distal end of the saw blade around its pivot axis.

A further preferred embodiment of the saw drive provides a first position for coupling a first pivot axis of a first saw blade of the set to the saw drive for obtaining a first pivot distance. The embodiment further provides a second position for coupling a second pivot axis of a second saw blade of the set to the saw drive for obtaining a second pivot distance.

A further preferred embodiment of the saw drive comprises a coupling mechanism with a first drive pin and a second drive pin. The first and the second drive pin are enclosable by a first and a second portion of a first slot arrangement of a first saw blade of the set. The first drive pin is configured to interlock with the first portion of the first slot arrangement of the first saw blade for transmitting the driving force of the saw drive to the first saw blade in a first force transmission point to obtain a first oscillation angle. The first and the second drive pin are further enclosable by a third and a fourth portion of a second slot arrangement of a second saw blade of the set, wherein the second drive pin is configured to interlock with the fourth portion of the second slot arrangement of the second saw blade for transmitting the driving force of the saw drive to the second saw blade in a second force transmission point to obtain a second oscillation angle.

In a further embodiment of the saw drive, the coupling mechanism comprises a drive pin for mating a slot of a saw blade of the set, wherein the drive pin, which preferably oscillates within a distance of 1-10 mm, is configured to convert a translational driving force parallel to a longitudinal axis from a proximal end to a distal end of the saw blade of the set into a rotation around the pivot axis.

Preferably for this embodiment, the drive pin of the saw drive is configured to couple to a slot in form of a recess, in particular a longitudinal recess, preferably extending to the proximal end of the saw blade. Preferably, the force transmission point is defined by an angle between a longitudinal axis of the recess and the longitudinal axis of the saw blade.

Further preferably for this embodiment, the mating slot is a curved recess, preferably extending to a proximal end of the saw blade, wherein a radius of the curved slot defines the force transmission point.

A further preferred embodiment of the present saw drive comprises a slot configured for mating with a first drive pin of a first saw blade of the set, wherein the first drive pin is positioned at a first pivot distance from the pivot axis, for obtaining a first oscillation angle. The slot is further configured for mating with a second drive pin of a second saw blade of the set, wherein the second drive pin is positioned at a second pivot distance from the pivot axis, for obtaining a second oscillation angle. Preferably, the saw drive comprises a rotating element which comprises the slot, for transmitting a rotational motion from the saw drive via the slot of the rotating element to the drive pin mating the slot.

In a further preferred embodiment the saw drive is couplable to each saw blade of the set of saw blades by means of a coupling mechanism comprising a saw blade guide for mating an outer contour of a saw blade of the set of saw blades, in particular wherein the outer contour is a circular section of the saw blade.

A further aspect of the invention refers to the use of the saw gear set as described above for surgery, in particular for osteotomy.

Other advantageous embodiments are listed in the dependent claims as well as in the description below.

BRIEF DESCRIPTION OF THE DRAWINGS

The invention will be better understood and objects other than those set forth above will become apparent from the following detailed description thereof. Such description makes reference to the annexed drawings, wherein.

MODES FOR CARRYING OUT THE INVENTION

Figure 1:
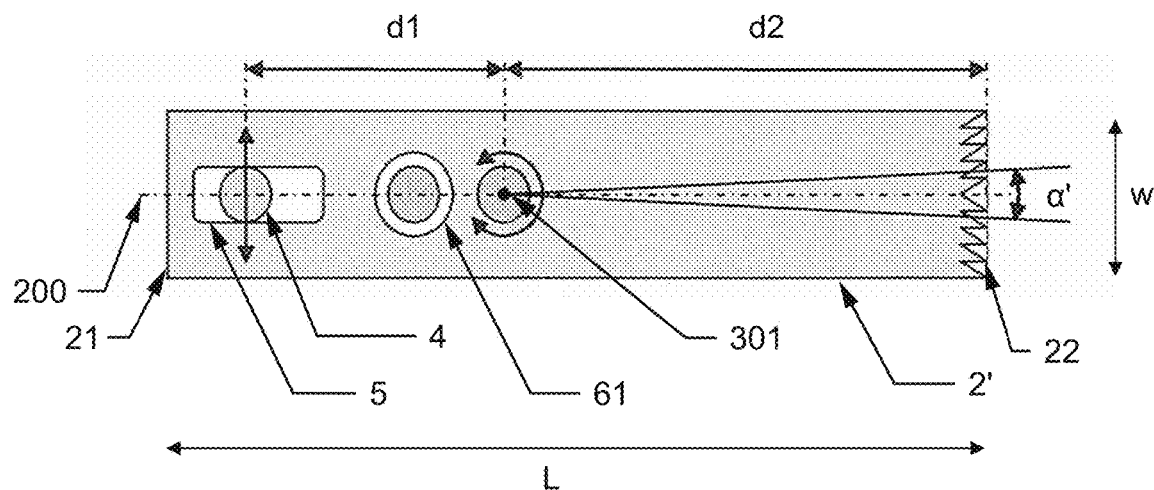
FIGS. 1 *a*) and *b*) show each a saw blade of a set of saw blades according to a preferred embodiment of the invention, FIG. 2 *a*) shows a saw blade of the set of FIG. 1 coupled to a saw drive and *b*) a cross section thereof, according to a preferred embodiment of the invention, FIGS. 3 *a*) and *b*) show each a saw blade of a set of saw blades according to a further preferred embodiment of the invention, FIG. 4 *a*) shows a saw blade of the set of FIG. 3 coupled to a saw drive and *b*) a cross section thereof, according to a preferred embodiment of the invention, FIG. 5 *a*) shows a saw blade of the set of FIG. 3 coupled to a saw drive and *b*) a cross section thereof, according to a preferred embodiment of the invention, FIGS. 6 *a*) and *b*) show each a saw blade of a set of saw blades according to a further preferred embodiment of the invention.
Figure 1:
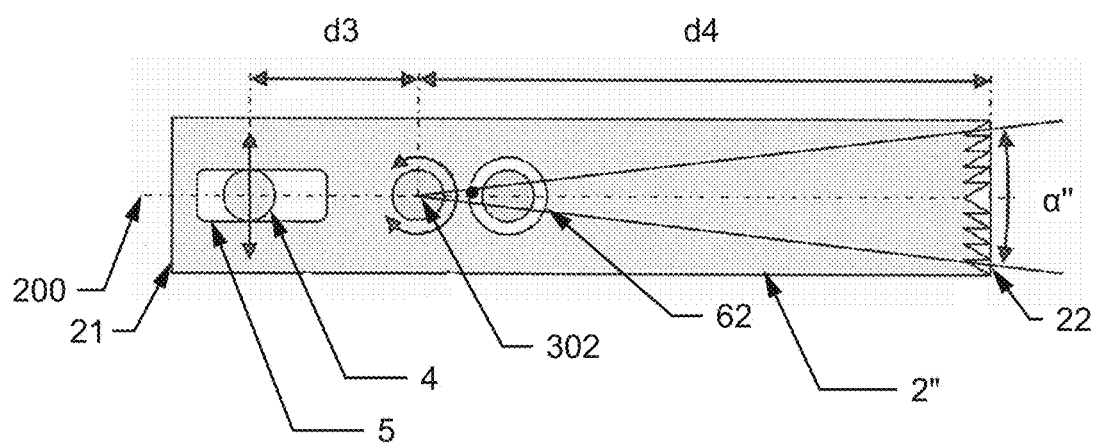

Preferred embodiments of the set of saw blades are shown in FIGS. 1, 3, 6, 7, and 9, wherein each saw blade is couplable to a saw 1 drive by means of a coupling mechanism 100, for transmitting a driving force from the saw drive 1 to the blade in a force transmission point, for oscillating the saw blade around a pivot axis 300.

A preferred coupling mechanism 100 comprises a drive pin 4 mating a slot 5.

Figure 10:
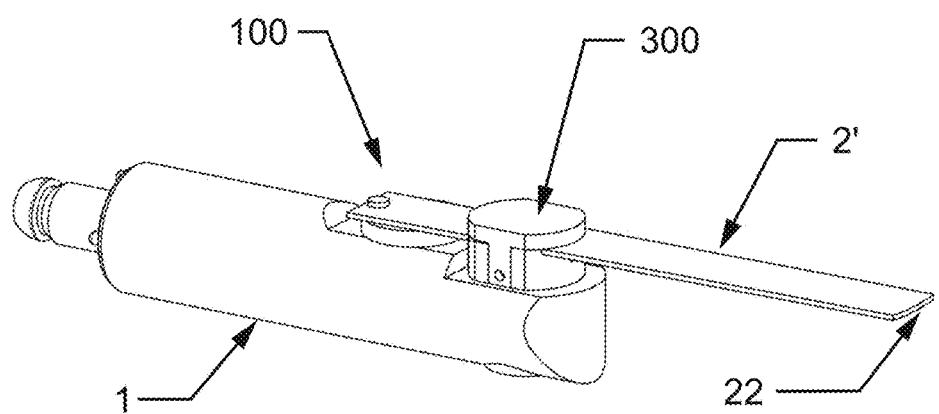
Figure 10:
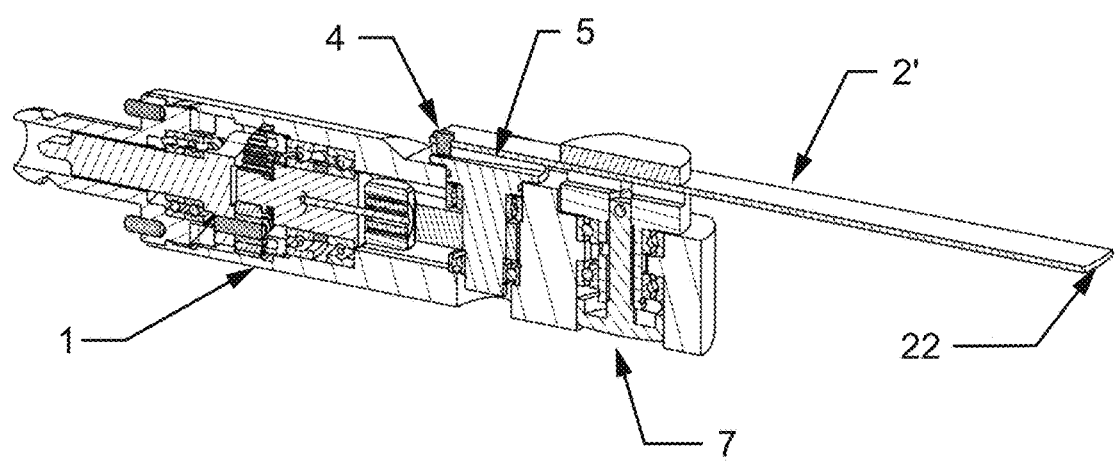

A further preferred coupling mechanism 100 comprises outer contour 44, in particular a circular section, in the saw blade mating a saw blade guide 55 of the saw drive 1 as shown in FIG. 10 a).

Each of the saw blades of the sets of the embodiments of the invention can be configured to be couplable to the saw drive 1 by either the coupling mechanism 100 comprising the drive pin 4 and the mating slot 5 or by the coupling mechanism comprising the outer contour 44 of a saw blade mating the saw blade guide 55 of the saw drive.

In addition, each saw blade of the set is pivotable mountable around a pivot axis 300.

In operation, an oscillation angle α around the pivot axis 300 is different for each saw blade of the set depending on a pivot distance between the pivot axis 300 and the force transmission point which varies for each saw blade of the set.

Preferably, the saw blades shown in the preferred embodiments of the figures have each a longitudinal axis 200 from a proximal end 21 to a distal end 22 of the blade. The proximal end 21 of each saw blade is preferably directed towards the saw drive 1 and the distal end 22 is directed away from the saw drive 1, preferably having the form of a serrated blade for sawing.

Preferably, the saw blades of the set are made of a material from the list of steel, spring steel and/or stainless steel.

A set of saw blades can comprise only one saw blade. Preferably, a set of saw blades comprises at least two saw blades with different pivot distances.

Preferably, each FIGS. 1, 3, 6, and 9 discloses each an embodiment of a set of saw blades comprising a first and a second saw blade. Preferably, FIG. 7 discloses an embodiment of a set of saw blades wherein only a first saw blade of the set is shown in the Figure. Furthermore, each saw blade of the embodiments of the set of saw blades shown in the FIGS. 1, 3, 6, 7, and 9 is in particular disclosed individually without being dependent on the respective set of saw blades.

Preferred embodiments of the saw drive 1 are shown in FIGS. 2, 4, 5, 8, 10, and 11 b) and c) wherein a first saw blade 2' from a set of saw blades is coupled to each of the embodiments of the saw drive 1. Each saw drive 1 of the figures is suitable to oscillate a saw blade, which is configured to be pivotably borne around a pivot axis 300. The saw drive 1 is couplable to a saw blade of the set of saw blades by means of the coupling mechanism 100, for transmitting a driving force from the saw drive to the blade in a force transmission point, wherein an oscillation angle α of the saw blade is different for each saw blade of the set, depending on the pivot distance between the force transmission point and the pivot axis of the saw blades, which varies for each saw blade of the set.

Preferably, the saw drive provides an oscillation center, for example a suspension or a clamp at the position of the pivot axis, to pivotably bear the saw blade around the pivot axis.

Preferably, the saw blade can be pivotably fastened to the saw drive at the position of the oscillation center.

FIG. 1 shows a preferred embodiment of the set of saw blades. FIG. 1 a) shows a first saw blade 2' and FIG. 1 b) a second saw blade 2" of the set of saw blades. The first 2' and the second 2" saw blade are preferably both of the same length L and the same width w. In a further embodiment, the first 2' and the second 2" saw blade can also be of different length and different width.

The saw blades 2', 2" of the set comprise a slot 5 mating a pin 4 of the saw drive 1, for coupling each saw blade 2', 2" of the set to the saw drive 1. Even though the drive pin 4 is pictured in FIG. 1, it is not part of the saw blades 2', 2" and only is imaged for elucidating the coupling mechanism. In addition, for illustration purposes, the arrows in FIGS. 1 a) and 1 b) indicate the motion of the drive pin 1 if coupled to the slot 5 of the saw blades 2', 2" in a translational direction perpendicular to the longitudinal axis of the saw blades 2', 2".

The first saw blade 2' has a first pivot axis 301 in a first position having a first pivot distance d1 to obtain a first oscillation angle α'. Preferably, if the first saw blade 2' is mounted to the saw drive 1, the first position of the first pivot axis 301 is aligned with a first oscillation center 71 of the saw drive 1, to pivotably bear the first saw blade 2' in regard of the saw drive 1.

The second saw blade 2" has a second pivot axis 302 in a second position having a second pivot distance d3 to obtain a second oscillation angle α". Preferably, if the second saw blade 2' is mounted to the saw drive 1, the second position of the second pivot axis 302 is aligned with a second oscillation center 72 of the saw drive, to pivotably bear the second saw blade 2' in regard of the saw drive 1.

The first saw blade 2' and the second saw blade 2" vary in their pivot distances d1 and d3 which are of different length. Preferably, the first pivot distance d1 is of greater length than the second pivot distance d3. Therefore, the first oscillation angle α' is smaller than the second oscillation angle α" and therefore the distal 22 end of the first saw blade 2' oscillates over a smaller arc length than the distal end 22 of the second saw blade 2".

A preferred saw drive 1 provides a first oscillation center 71 in the first position for pivotably bear the first saw blade 2' around the first pivot axis 301 and a second oscillation center 72 in the second position for pivotably bear the second saw blade 2" around the second pivot axis 302.

Therefore, the first saw blade 2' preferably comprises a first recess 61 in the second position, for exempting the second oscillation center 72 of the saw gear 1. Due to the presence of the second oscillation center 72, the first saw blade 2' comprises the first recess 61 in the second position of the second pivot axis 302, which recess is large enough to enclose the second oscillation center 72 such that the first saw blade 2' is not obstructed by the second oscillation center 72 in its oscillation around the first pivot axis 301 in the first oscillation center 71.

The second saw blade 2" preferably comprises a second recess 62 in the second position, for exempting the first oscillation center 71 of the saw gear 1.

Due to the presence of the first oscillation center 71, the second saw blade 2" comprises the second recess 62 in the first position of the first pivot axis 301, which recess is large enough to enclose the first oscillation center 71 such that the second saw blade 2" is not obstructed by the first oscillation center 71 in its oscillation around the second pivot axis 302 in the second oscillation center 72.

Figure 2:
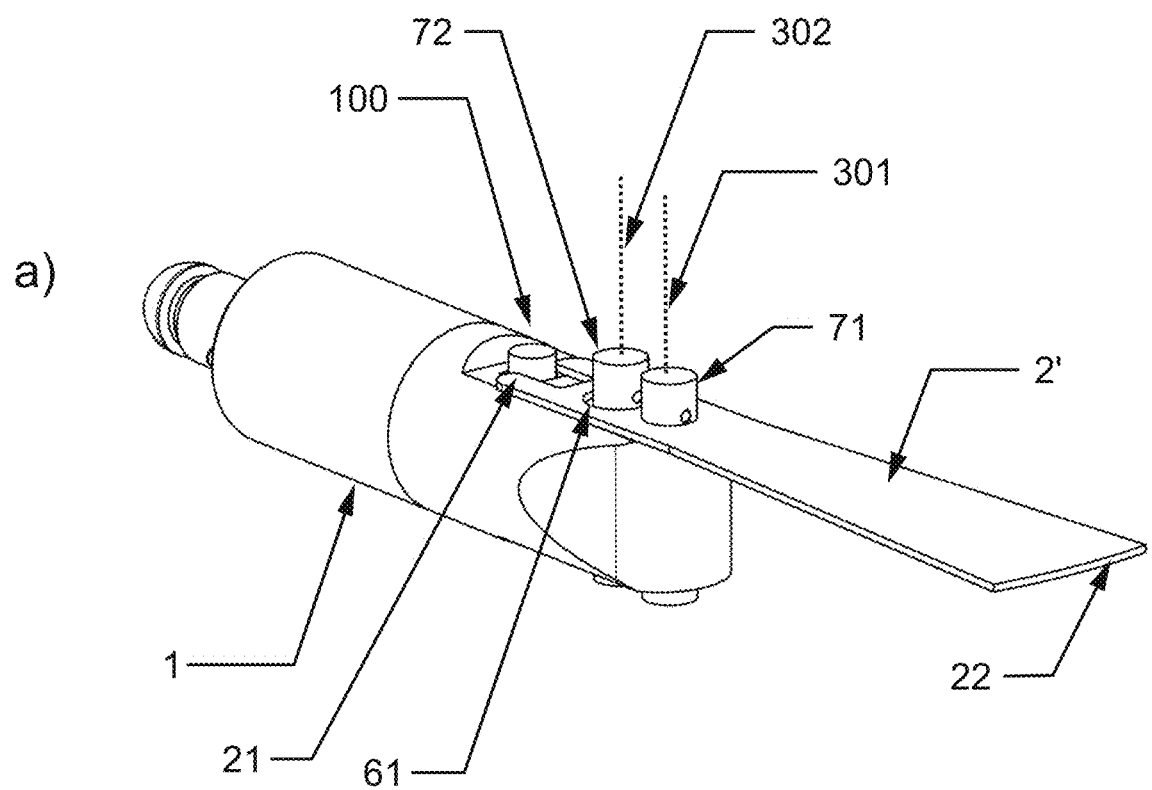
Figure 2:
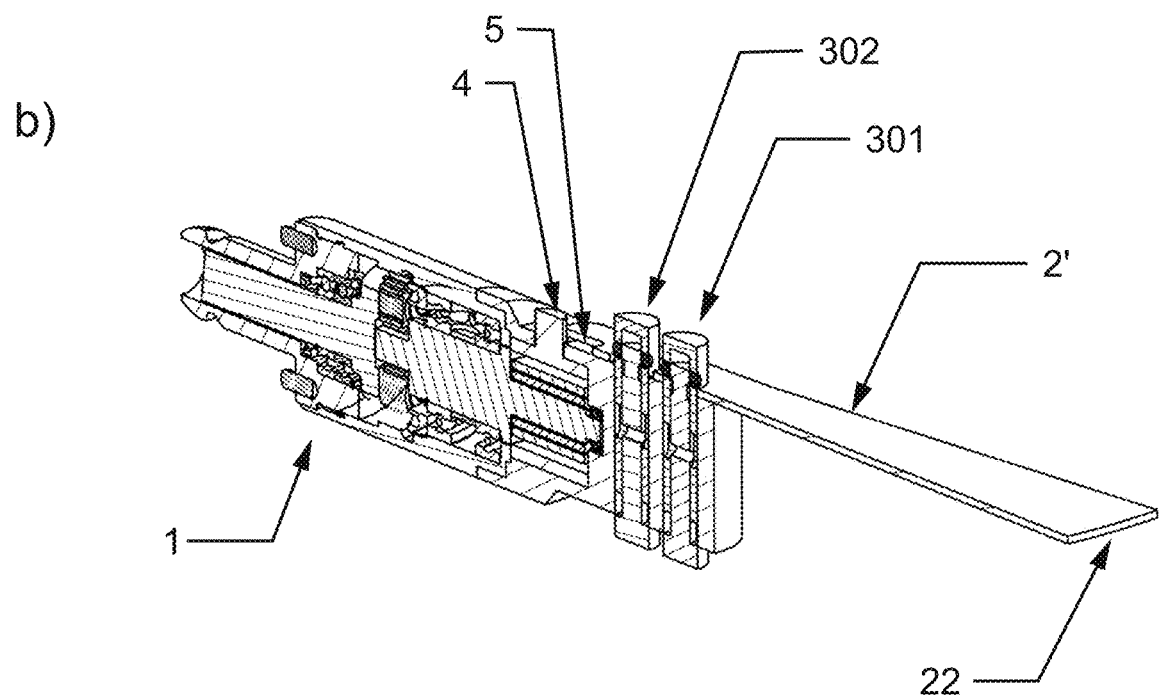

FIG. 2 *a*) shows the saw drive providing a first 71 and a second 72 oscillation center to pivotably bear a saw blade of the set from FIG. 1 around a first pivot axis 301 or around a second pivot axis 302.

In FIG. 2 *a*), as an example, the first saw blade 2' of the set of FIG. 1 is shown to be coupled to the saw drive 1 by means of a coupling mechanism 100. For this embodiment of the first saw blade, the slot 5 opens to the proximal end 21 of the saw blade.

The first saw blade 2' is configured to be pivotably borne around a first pivot axis 301 in the first oscillation center 71 of the saw drive.

Due to the presence of the second oscillation center 72, the first saw blade 2' comprises the first recess 61 in the second position of the second pivot axis 302, which recess is large enough to enclose the second oscillation center 72 such that the first saw blade 2' is not obstructed by the second oscillation center 72 in its oscillation around the first pivot axis 301 in the first oscillation center 71.

FIG. 2 *b*) shows the cross section of the saw drive 1 with the first saw blade 2' of FIG. 2 *a*). The driving force of the saw drive 1 is transmitted to the saw blade by the coupling mechanism 100. Preferably, as shown in FIG. 2 *b*), the coupling mechanism 100 comprises the drive pin 4 mating the slot 5. The force transmission point is the point, where the pin 4 transmits a translational force to the slot 5 and therefore to the saw blade. In the embodiment shown in FIG. 2 *b*), the drive pin 5 experiences a translational motion from the saw drive 1 and therefore transmits a translational driving force to the blade 2' in a direction, which is perpendicular to the longitudinal axis 200 from the proximal end 21 to the distal end 22 of the first saw blade 2' and perpendicular to the first pivot axis 301. The translational driving force is thereby translated into a rotation of the distal end 22 of the saw blade around its first pivot axis 301.

Figure 3:
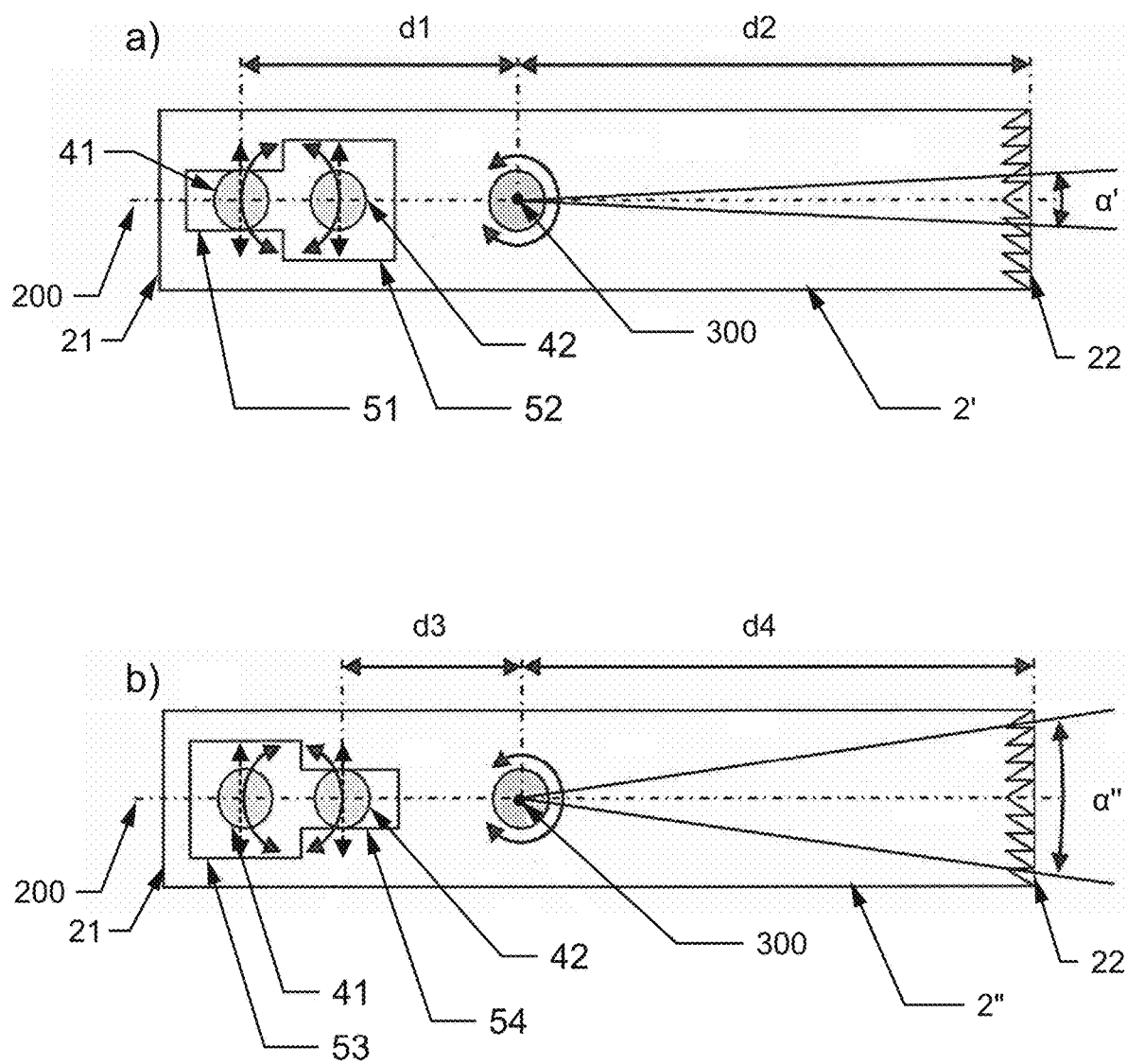

FIG. 3 shows a further preferred embodiment of the set of saw blades. FIG. 3 *a*) shows a first saw blade 2' and FIG. 3 *b*) a second saw blade 2" of the set of saw blades. The first 2' and the second 2" saw blade are preferably both of the same total length L and the same width w. In a further embodiment, the second saw blade 2" might be shorter and of different width than the first saw blade 2'.

The first saw blade 2' as shown in FIG. 3 *a*) comprises a first slot arrangement with a first portion 51 and a second portion 52, which first slot arrangement is configured to enclose a first 41 and a second 42 drive pin of the saw drive 1. The first drive pin 41 interlocks with the first portion 51 of the first slot arrangement, for transmitting the driving force of the saw drive 1 to the first saw blade 2' in a first force transmission point to obtain a first oscillation angle α'.

The first portion 51 and the second portion 52 have each the form of a squared portion which are in connection with each other. Preferably, the cross section area of the second portion 52 is twice the cross section area of the first portion 51, very preferably three times the cross section area of the first portion 51.

The second saw blade 2" as shown in FIG. 3 *b*) comprises a second slot arrangement with a third portion 53 and a fourth portion 54, which second slot arrangement encloses the first 41 and the second 42 drive pin. The second drive pin 42 interlocks with the fourth portion 54 of the second slot arrangement, for transmitting the driving force of the saw drive 1 to the second saw blade 2" in a second force transmission point to obtain a second oscillation angle α".

The third portion 53 and the fourth portion 54 have each the form of a squared portion which are in connection with each other. Preferably, the cross section area of the third portion 53 is twice the cross section area of the fourth portion 54, very preferably three times the cross section area of the fourth portion 54.

Even though the first and the second drive pins 41, 42 are pictured in FIG. 3, they are not part of the saw blades 2', 2" and only are imaged for elucidating the coupling mechanism. In addition, for illustration purposes, the semicircle arrows in FIGS. 3 *a*) and *b*) related to the first 41 and the second 42 drive pin indicate the moving direction of the pins in a rotational direction. The dotted arrows in FIGS. 3 *a*) and *b*) related to the first 41 and the second 42 drive pin indicate the moving direction of the pins in a translational direction.

The saw drive 1 of the embodiment shown in FIGS. 3 *a*) and 3 *b*) comprises the first 41 and the second 42 drive pin, but preferably contains only one oscillation center to pivotably bear the saw blades at the position of the pivot axis 300, which is the same position for the first blade 2' and the second blade 2".

Figure 4:
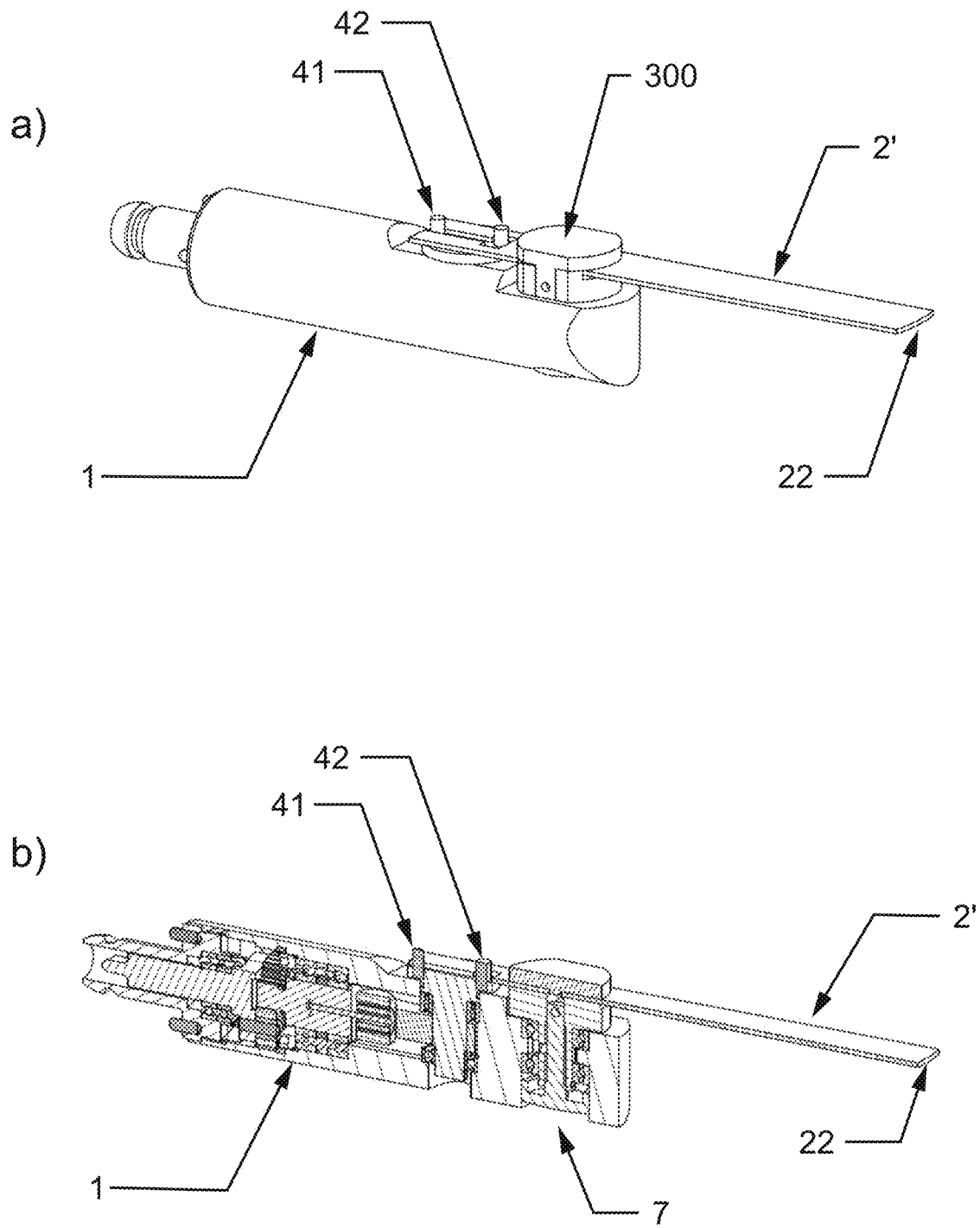

FIG. 4 *a*) shows the saw drive providing a first 41 and a second 42 drive pin for mating the slot of the first saw blade 2' of the set of FIG. 3 as an example.

As shown in FIG. 4 *a*), the slot 5, in particular the first portion 51 of the slot 5, can open to the distal end 21 of the saw blade 2'.

The first saw blade 2' is configured to be pivotably borne around a pivot axis 300 in the oscillation center 7 of the saw drive 1. Preferably, the oscillation center 7 of the saw drive is at the same position for all the saw blades of the set. Therefore, the oscillation angle of each saw blade of the set varies preferably by solely adjusting the first 51, second 52, third 53, and fourth 54 portion of the respective slot.

FIG. 4 *b*) shows the cross section of FIG. 4 *a*). The driving force of the saw drive 1 is transmitted to the first saw blade 2' by the coupling mechanism 100. Preferably, as shown in FIG. 4 *b*), the coupling mechanism 100 comprises the first slot arrangement enclosing the first drive pin 41 and the second drive pin 42 of the saw drive. The first drive pin 41 interlocks with the first portion 51 of the first slot arrangement, for transmitting the driving force of the saw drive 1 to the first saw blade 2' in a first transmission point to obtain a first oscillation angle α'.

The force transmission point between the first drive pin 41 and the first portion 51 is the point, where the pin 41 transmits a driving force to the slot 5 in a first portion 51 thereof and therefore to the first saw blade 2'. The driving force acts as a rotational force on the first 41 and the second 42 drive pin, such that the first drive pin 41, which is interlocked with the first portion 51 of the slot, transmits the rotational force to the first saw blade 2', where the rotational force is translated into a rotation of the distal end 21 of the first saw blade 2' around its pivot axis 300. As a result, the first saw blade 2' oscillates, preferably within an angle of 1-10°, around the pivot axis 300. The second drive pin 42 is rotated with the first drive pin 41, but due to the larger cross-section area of the second portion 52 of the slot, the second drive pin 42 does not interlock with the first saw blade 2' and therefore does not transmit any force to the saw blade 2', but oscillates freely within the second portion 52.

Figure 5:
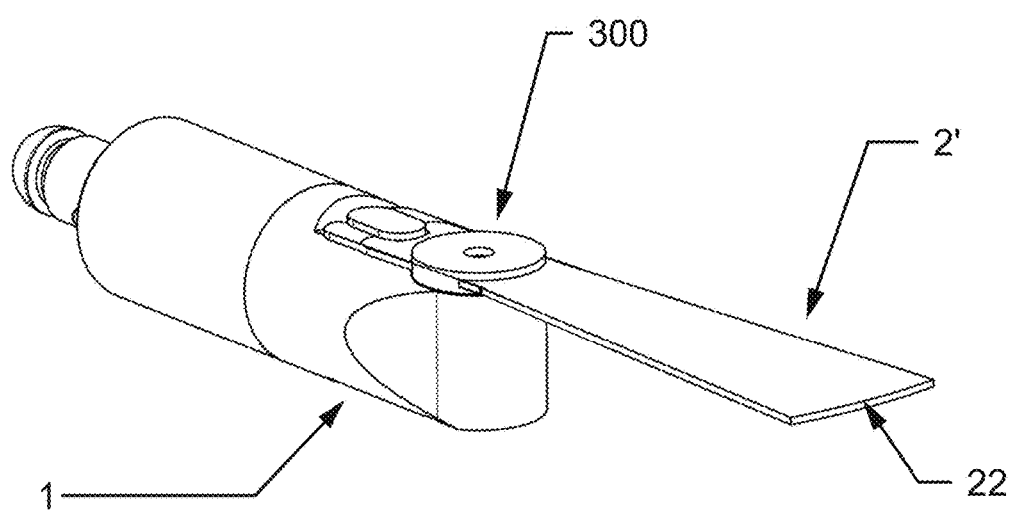
Figure 5:
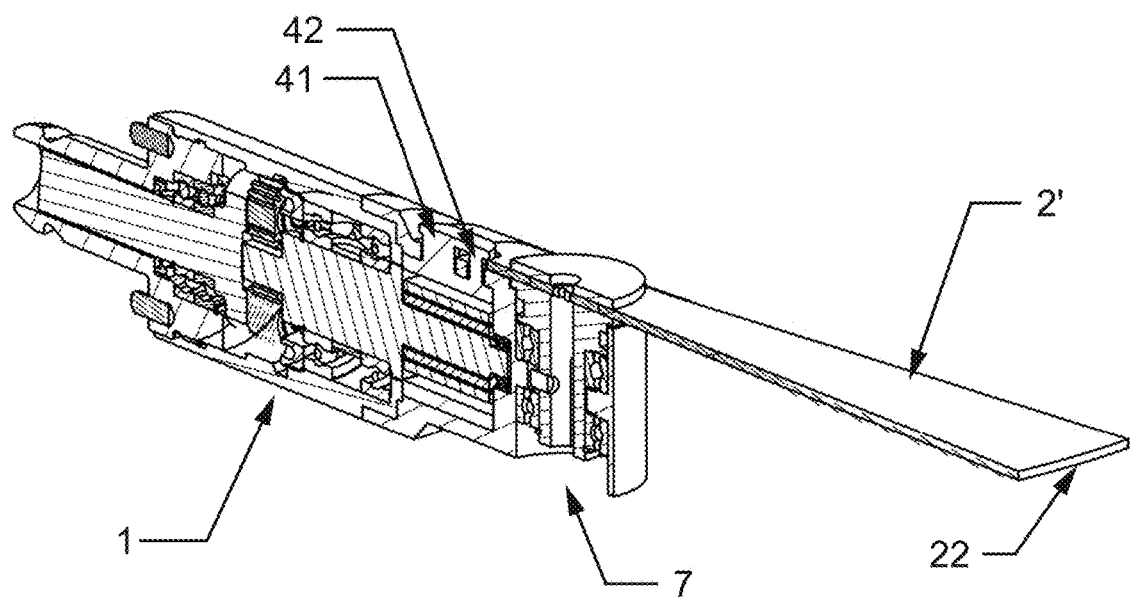

In FIG. 5 a) shows a further embodiment of a saw drive 1, providing a first 41 and a second 42 drive pin for mating the slot of the first saw blade 2' of the set of FIG. 3 as an example.

As shown in FIG. 5 a), the slot 5, in particular the first portion 51 of the slot 5, can open to the distal end 21 of the saw blade 2'.

The first 41 and the second 42 drive pin can be formed from one piece.

The first saw blade 2' is configured to be pivotably borne around a pivot axis 300 in the oscillation center 7 of the saw drive 1. Preferably, the oscillation center 7 of the saw drive is at the same position for all the saw blades of the set. Therefore, the oscillation angle of each saw blade of the set varies preferably by solely adjusting the first 51, second 52, third 53, and fourth 54 portion of the respective slot.

FIG. 5 b) shows the cross section of the saw drive 1 with the first saw blade 2' of FIG. 5 a). The driving force of the saw drive 1 is transmitted to the saw first blade 2' by the coupling mechanism 100. Preferably, as shown in FIG. 5 b), the coupling mechanism 100 comprises the first slot arrangement enclosing the first drive pin 41 and the second drive pin 42 of the saw drive. The first drive pin 41 interlocks with the first portion 51 of the first slot arrangement, for transmitting the driving force of the saw drive 1 to the first saw blade 2' in a first transmission point to obtain a first oscillation angle α'.

The force transmission point between the first drive pin 41 and the first portion 51 is the point, where the pin 41 transmits a driving force to the slot 5 in a first portion 51 thereof and therefore to the first saw blade 2'. The driving force acts as a translation force on the first 41 and the second 42 drive pin, such that the first drive pin 41, which is interlocked with the first portion 51 of the slot, transmits the translational force to the first saw blade 2', in a direction which is perpendicular to the longitudinal axis 200 of the first saw blade 2'. The translational driving force is translated into a rotation of the distal end 21 of the first saw blade 2' around its pivot axis 300. As a result, the first saw blade 2' oscillates around the pivot axis 300. The second pin 42 is translated, but due to the larger cross-section area of the second portion 52, does not interlock with the first saw blade 2' and therefore does not transmit any force to the saw blade 2', but oscillates freely within the second portion 52.

Figure 6:
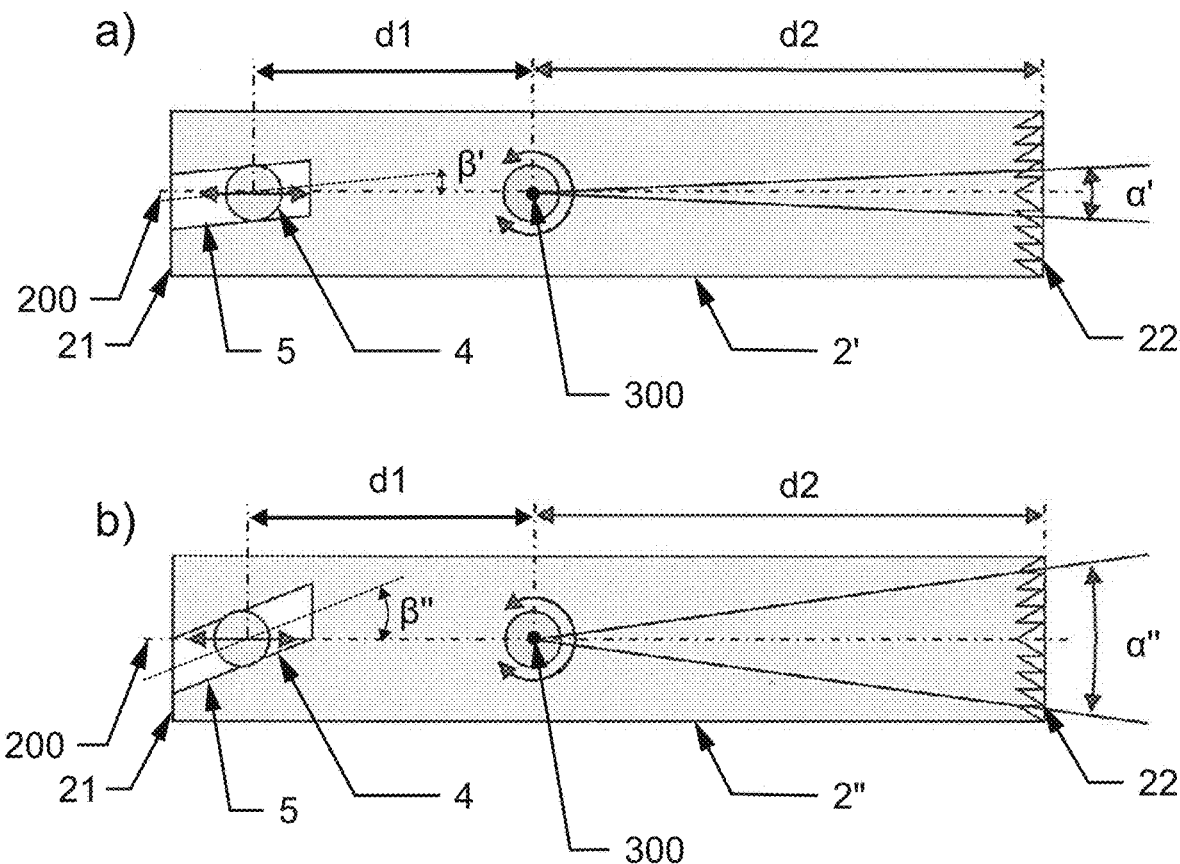

FIG. 6 shows a further preferred embodiment of a set of saw blades according to the invention. FIG. 6 a) shows a first saw blade 2', and FIG. 6 b) shows a second saw blade 2" of the set. The saw blades 2', 2" each comprise a slot 5 in the form of a longitudinal recess, which slot is configured to enclose the drive pin 4 of the saw drive 1. The slot 5 preferably extends to the proximal 21 end of each saw blade 2', 2", very preferably opens to the proximal end 21 of each saw blade 2', 2". As shown in FIG. 6 a), a first angle α' between a longitudinal axis of a first recess of a first saw blade 2' of the set and the longitudinal axis 200 of the first saw blade 2' defines a first force transmission point for a drive pin 4 transmitting a driving force to the first saw blade 2' in a direction parallel to the longitudinal axis 200, to obtain a first oscillation angle α' around the pivot axis 300.

As shown in FIG. 6 b), a second angle (3" between a longitudinal axis of a second recess and the longitudinal axis 200 of a second saw blade 2" defines a second force transmission point for a drive pin 4 transmitting a driving force to the second saw blade 2" in a direction parallel to the longitudinal axis 200, to obtain a second oscillation angle α" around the pivot axis 300.

Figure 7:
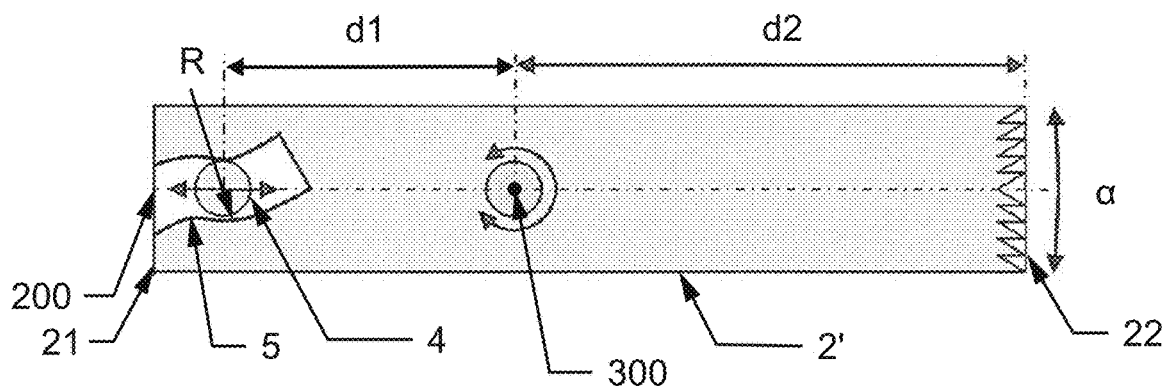
FIG. 7 shows a saw blade of a set of saw blades according to a further preferred embodiment of the invention, FIG. 8 a) shows a saw blade of the set of FIG. 6 coupled to a saw drive and b) a cross section thereof, according to a preferred embodiment of the invention, FIGS. 9 a) and b) show each a saw blade of a set of saw blades according to a further preferred embodiment of the invention, FIG. 10 a) shows a saw blade of the set of FIG. 9 coupled to a saw drive and b) a cross section thereof, according to a preferred embodiment of the invention, FIGS. 11 a) and b) show different views of a saw drive with a saw blade of a set coupled and a saw drive, wherein the saw blade is coupled to the saw drive, wherein the coupling mechanism comprises an outer contour of the saw blade mating a saw blade guide of the saw drive according to an embodiment of the invention.

FIG. 7 shows a further preferred embodiment of a first saw blade 2' of a set of saw blades according to the invention. The slot 5 is a curved recess, preferably opens to the proximal end 21 of the saw blade 2', wherein a radius R of the curved slot 5 defines the force transmission point for a drive pin 4 transmitting a driving force to the first saw blade 2' in a direction parallel to the longitudinal axis 200, to obtain the oscillation angle α' around the pivot axis 300. Preferably, a second saw blade of the set, which is not shown, could comprise a second curved recess, wherein a Radius of the curved recess defines a second force transmission point for the second saw blade.

Figure 8:
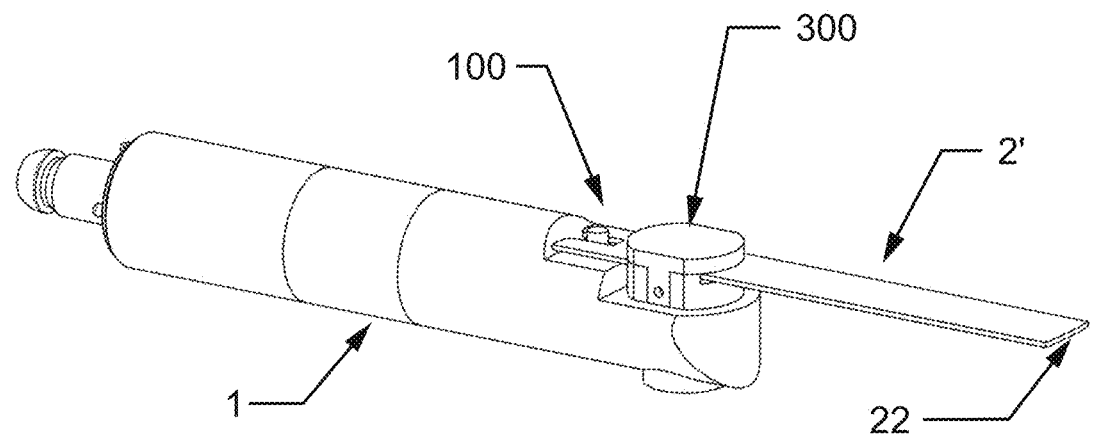
Figure 8:
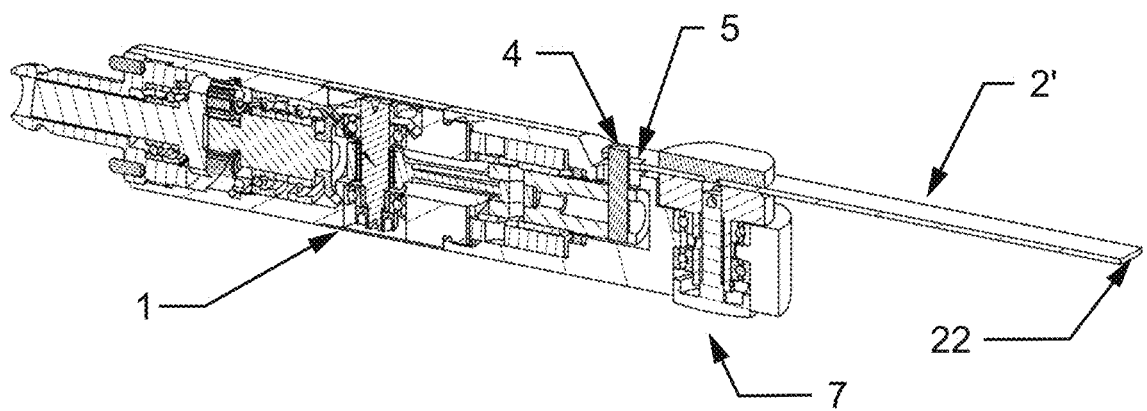

FIG. 8 a) shows a further embodiment of a saw drive 1 with a oscillation center 7 to pivotably bear a saw blade of the set from FIG. 6 or FIG. 7, for example the first saw blade 2' of FIG. 6 a), which is coupled to the saw drive 1 by means of a coupling mechanism comprising the drive pin 4 and the first recess.

Preferably, the oscillation center 7 is at the same position for all the saw blades of the set.

FIG. 8 b) shows a cross-section of the saw drive 1 and the first saw blade 2' of FIG. 8 a). The driving force is acting on the saw blade in a direction parallel to the longitudinal direction 200 of the saw blade 2' and preferably oscillates within a distance of 1-10 mm back and forth. The driving force is translated into a rotation of the distal end 22 of the saw blade 2' around its pivot axis 300.

Figure 9:
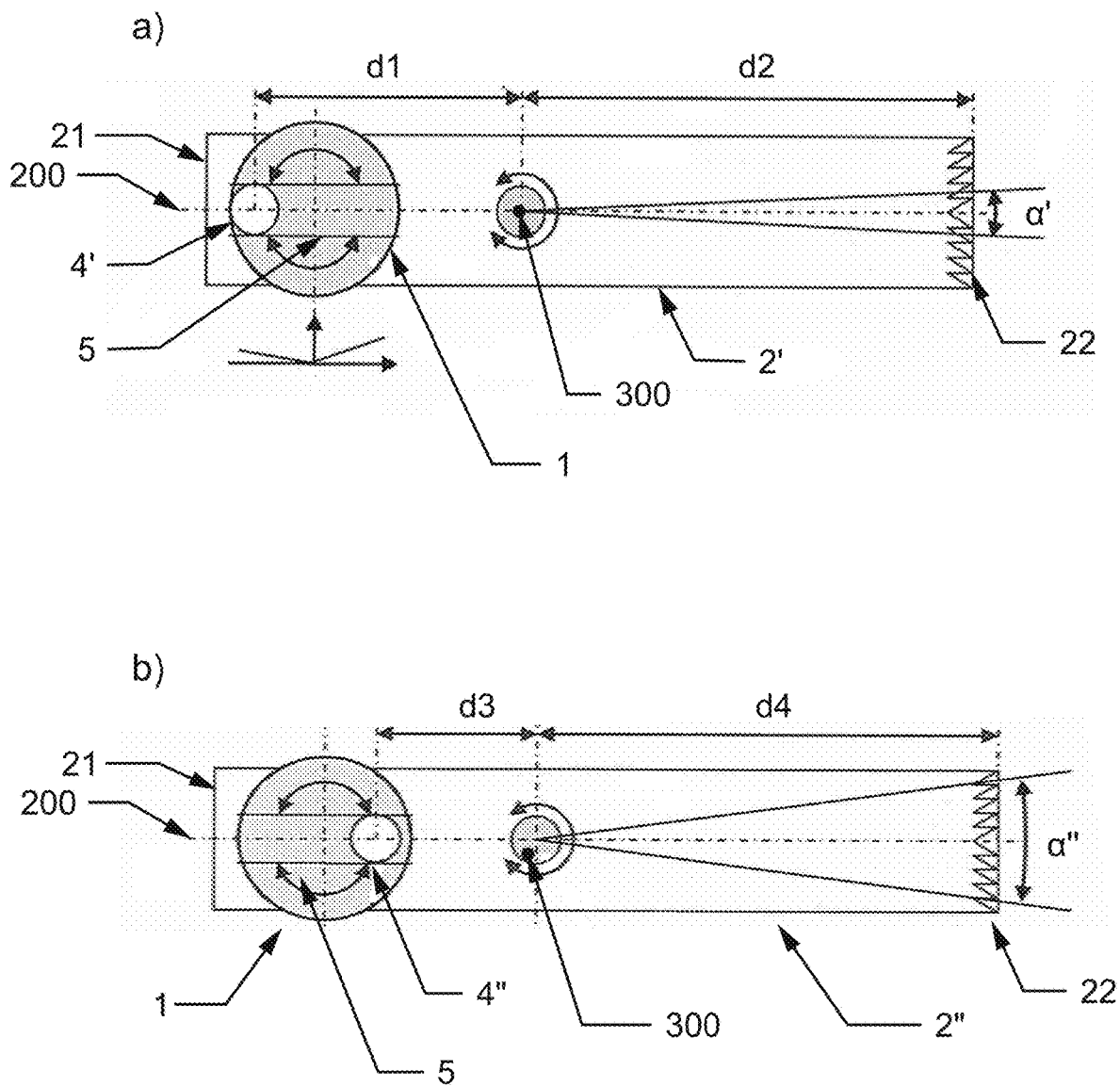

FIG. 9 shows a further preferred embodiment of the set of saw blades. FIG. 9 a) shows a first saw blade 2' and FIG. 9 b) shows a second saw blade 2" of the set of saw blades. The first 2' and the second 2" saw blades are preferably both of the same length L and width w. In a further preferred embodiment, the first 2' and the second 2" saw blade might be of different length and width.

The saw blades 2', 2" of the set comprise a pin 4 mating a slot 5 of the saw drive 1, for coupling each saw blade 2', 2" of the set to the saw drive 1. Even though the slot 5 is pictured in FIG. 1, it is not part of the saw blades 2', 2" and only is imaged for elucidating the coupling mechanism.

The coupling mechanism 100 comprises a drive pin 4 mating a slot 5, wherein the saw drive 1 comprises the slot 5 and wherein the first saw blade 2' of the set comprises a first drive pin 4' positioned at a first pivot distance d1 from the pivot axis 300 to obtain a first oscillation angle α'. The second saw blade 2" of the set comprises a second drive pin 4" positioned at a second pivot distance d3 from the pivot axis 300 to obtain a second oscillation angle α".

Preferably, the first pivot distance d1 is larger than the second pivot distance d2 and therefore the first oscillation angle α' is smaller than the second oscillation angle α".

In addition, for illustration purposes, the semicircle arrows in FIGS. 9 a) and b) indicate the moving direction of the slot 5 in a rotational direction.

The first and the second saw blades 2',2" have each a pivot axis 300 in a position of a respective pivot distance d1 to obtain the respective oscillation angle α', α". Preferably, if the first 2' or second 2" saw blade is mounted to the saw drive 1, the position of the pivot axis 300 is aligned with the oscillation center of the saw drive 1, to pivotably bear the first 2' or second 2" saw blade in regard of the saw drive 1.

FIG. 10 a) shows an example of the first saw blade 2' of FIG. 9 a) coupled to the saw drive 1. FIG. 10 b) shows a cross-section of the saw drive 1 and the first saw blade 2' of FIG. 10 a). The force transmission point is between the first drive pin 4' and slot 5, wherein the slot 5 transmits the driving force to the pin 4'. The driving force acts as a rotational force on the slot 5, such that the slot, which mates the first drive pin 4', transmits the rotational force to the first saw blade 2', where the rotational force is translated into a rotation of the distal end 21 of the first saw blade 2' around its pivot axis 300. Preferably, the saw drive 1 comprises a rotating element which comprises the slot 5, for transmitting a rotational motion from the saw drive 1 via the slot 5 of the rotating element to the drive pin 4' of the saw blade 2', which is mating the slot 5.

The saw drive 1 preferably comprises an oscillation center 7 to pivotably bear a saw blade of the set from FIG. 9, for example the first saw blade 2' of FIG. 9 a), which is coupled to the saw drive 1 by means of a coupling mechanism comprising the drive pin 4 and the slot 5.

Preferably, the oscillation center 7 is at the same position for all the saw blades of the set.

Figure 11:
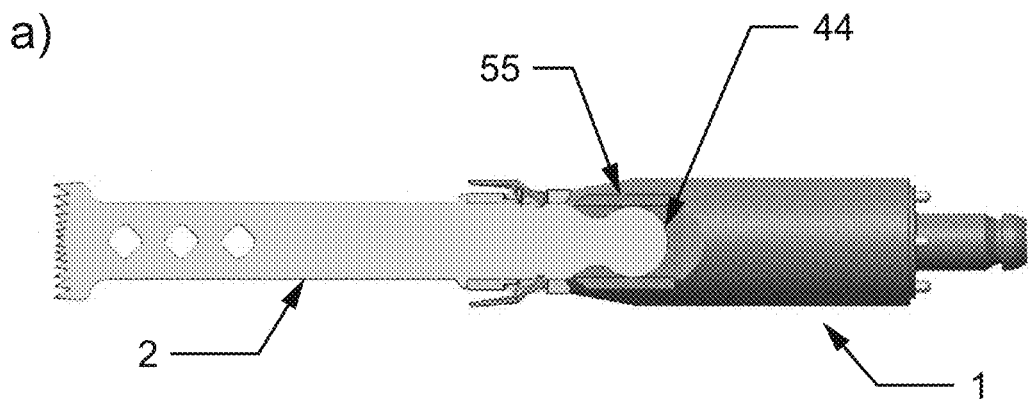
FIG. 11 c) shows a cross section the embodiment of FIG. 11 b).
Figure 11:
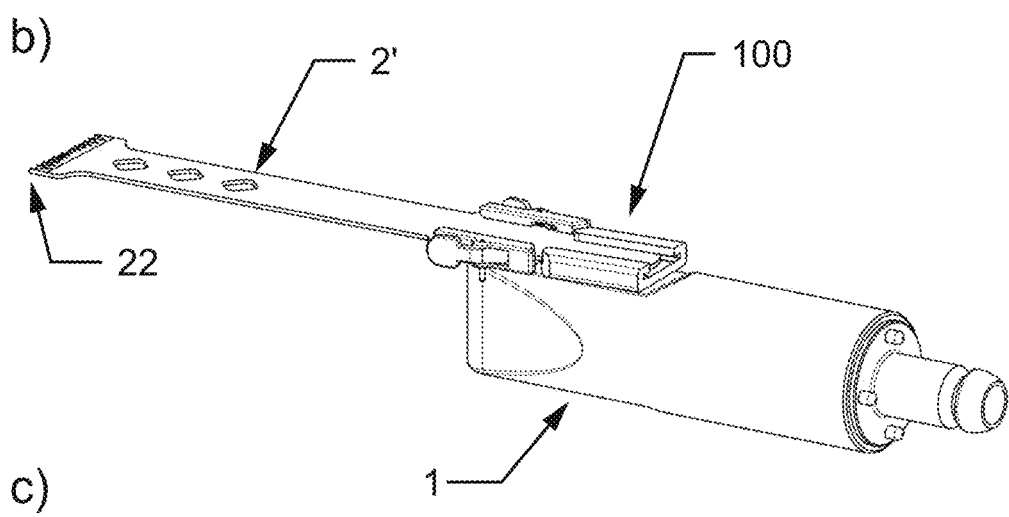
Figure 11:
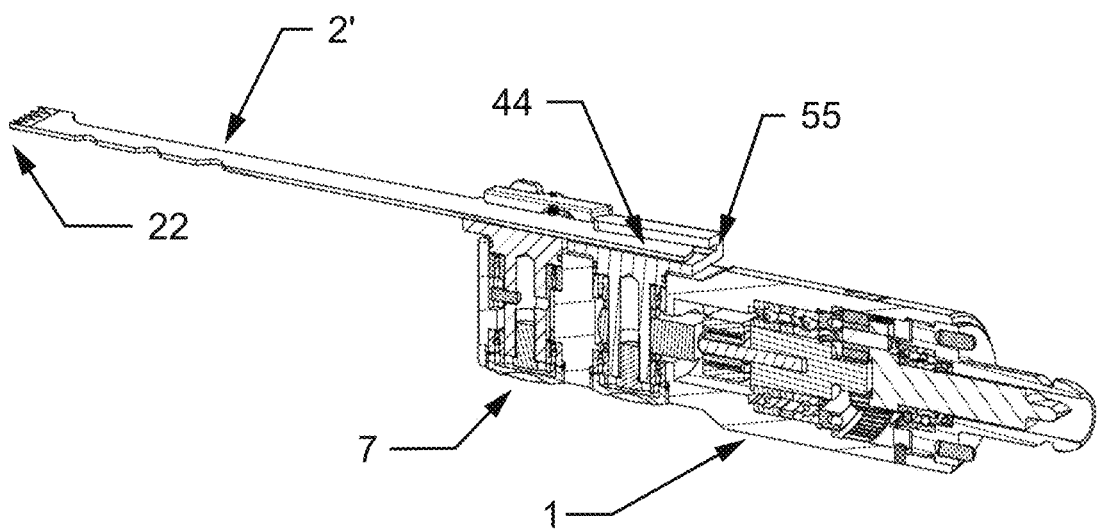

FIG. 11 shows a further preferred coupling mechanism 100 of the saw blades of the set of saw blades.

FIG. 11 a) shows a saw blade 2 of the set coupled to the saw drive 1, wherein the saw blade 2 can represent any one of the saw blades of the sets as shown or described in the previous figures or embodiments of the invention, but replacing the coupling mechanism comprising the drive pin 4 mating a slot 5 of the previous embodiments by an outer contour 44 of the saw blade mating a blade guide 55 of the saw drive 1. In particular the set of saw blades of FIG. 1 and FIG. 9 can comprise the coupling mechanism 100 comprising the outer contour 44 of the saw blade mating a blade guide 55. The saw blade shown in FIG. 11 a) comprises the outer contour 44 configured for mating the saw blade guide 55. In particular, the outer contour has the form of a circular section, which can rotate within the saw blade guide 55, even though it is fixed in a direction of the pivot axis 300 such that the saw blade can oscillate around the pivot axis 300.

The oscillation center 7 of the embodiment in FIG. 11 is defined by the clamps fixing the saw blade such that it can only rotate around a pivot axis 300 defined by the position where the clamps engage with the blade.

FIG. 11 b) shows the saw drive providing the oscillation center to pivotably bear the saw blade, preferably fixed to the saw blade at the position of the oscillation center.

FIG. 11 c) shows the cross section of the saw drive 1 with the saw blade of FIG. 11 b). The driving force of the saw drive 1 is transmitted to the saw blade by the coupling mechanism 100. The force transmission point is the point, where the blade guide 55 transmits a rotational force to the outer contour 44 of the blade and therefore to the saw blade 2. In the embodiment of FIG. 11 c), the blade guide 55 experiences a rotational motion from the saw drive 1, and therefore transmits a rotational driving force to the blade 2. The rotational force is thereby translated into a rotation of the distal end 22 of the saw blade 2 around its pivot axis 300.

The position of the force transmission point depends on the shape of the outer contour 44 of the saw blade. The oscillation angle α depends on the distance between the pivot axis 300 and the force transmission point. Therefore, the oscillation angle α for this coupling mechanism can be tuned by either adjusting the shape of the outer contour 44 of the saw blade or by adjusting the position of the pivot axis 300.

Identical elements are referred to by the same reference numerals in all Figures.

The invention claimed is:

1. A saw drive for oscillating a saw blade of a set of saw blades, wherein the saw blade is configured to be pivotably borne around a pivot axis,
    wherein the saw drive is couplable to the saw blade by means of a coupling mechanism, the coupling mechanism comprising a drive pin mating a slot, wherein the coupling mechanism is configured to transmit a driving force of the saw drive to the saw blade in a force transmission point,
    wherein an oscillation angle of the saw blades of the set is different for each saw blade, depending on a pivot distance between the force transmission point and the pivot axis of the respective saw blade, which varies for each saw blade of the set,
    the saw drive comprising a slot configured for mating with a first drive pin of a first saw blade of the set, wherein the first drive pin is positioned at a first pivot distance from the pivot axis, for obtaining a first oscillation angle (α'), and
    wherein the slot is further configured for mating with a second drive pin of a second saw blade of the set, wherein the second drive pin is positioned at a second pivot distance from the pivot axis, for obtaining a second oscillation angle (α").

2. The saw drive according to claim 1 configured to apply the driving force as a rotational force, oscillating within 1°-10° around a pivot axis, to a saw blade of the set of saw blades, wherein the driving force is translated into a rotation of a distal end of the saw blade around its pivot axis.

3. The saw drive according to claim 1 configured to apply a driving force as a translational force acting on a saw blade of the set of saw blades in a direction perpendicular to a longitudinal axis from a proximal end to a distal end of the saw blade and perpendicular to the pivot axis,
    wherein the driving force is translated into a rotation of the distal end of the saw blade around its pivot axis.

4. The saw drive according to claim 1 providing
    a first position for coupling a first pivot axis of a first saw blade of the set to the saw drive for obtaining a first pivot distance, and
    a second position for coupling a second pivot axis of a second saw blade of the set to the saw drive for obtaining a second pivot distance.

5. A saw drive for oscillating a saw blade of a set of saw blades, wherein the saw blade is configured to be pivotably borne around a pivot axis,
    wherein the saw drive is couplable to the saw blade by means of a coupling mechanism, the coupling mechanism comprising, a drive pin mating a slot, wherein the coupling mechanism is configured to transmit a driving force of the saw drive to the saw blade in a force transmission point,
    wherein an oscillation angle of the saw blades of the set is different for each saw blade, depending on a pivot distance between the force transmission point and the pivot axis of the respective saw blade, which varies for each saw blade of the set;
    wherein the saw drive comprises a first drive pin and a second drive pin,
    wherein the first and second drive pins are enclosable by first and second portions, of a first slot arrangement of a first saw blade of the set,
    wherein the first drive pin is configured to interlock with the first portion of the first slot arrangement of the first saw blade for transmitting the driving force of the saw drive to the first saw blade in a first force transmission point to obtain a first oscillation angle ($\alpha'$), and wherein the first and second drive pins are further enclosable by third and fourth portions of a second slot arrangement of a second saw blade of the set, wherein the second drive pin is configured to interlock with the fourth portion of the second slot arrangement of the second saw blade for transmitting the driving force of the saw drive to the second saw blade in a second force transmission point to obtain a second oscillation angle ($\alpha''$).

6. A saw drive for oscillating a saw blade of a set of saw blades, wherein the saw blade is configured to be pivotably borne around a pivot axis, wherein the saw drive is couplable to the saw blade by means of a coupling mechanism, the coupling mechanism comprising a drive pin mating a slot, wherein the coupling mechanism is configured to transmit a driving force of the saw drive to the saw blade in a force transmission point, wherein an oscillation angle of the saw blades of the set is different for each saw blade, depending on a pivot distance between the force transmission point and the pivot axis of the respective saw blade, which varies for each saw blade of the set;

the saw drive comprising the drive pin for mating with the slot of the saw blade the set, wherein the drive pin, oscillates within a distance of 1-10 mm, and is configured to convert a translational driving force parallel to a longitudinal axis from a proximal end to a distal end of the saw blade of the set into a rotation around the pivot axis, wherein the drive pin of the saw drive is configured to couple to the slot in form of a longitudinal recess; and wherein the force transmission point is defined by an angle between a longitudinal axis of the recess and the longitudinal axis of the saw blade.

7. The saw drive according to claim 6, wherein the slot is a curved recess, wherein a radius of the curved recess defines the force transmission point.

* * * * *